(12) United States Patent
Schneider

(10) Patent No.: US 12,599,745 B2
(45) Date of Patent: Apr. 14, 2026

(54) HINGED LID FOLDING BOX FOR CATHETER SYSTEMS

(71) Applicant: BIOTRONIK AG, Buelach (CH)

(72) Inventor: Bjoern Schneider, Zurich (CH)

(73) Assignee: BIOTRONIK AG, Buelach (CH)

( * ) Notice: Subject to any disclaimer, the term of this patent is extended or adjusted under 35 U.S.C. 154(b) by 57 days.

(21) Appl. No.: 18/713,925

(22) PCT Filed: Nov. 28, 2022

(86) PCT No.: PCT/EP2022/083479
§ 371 (c)(1),
(2) Date: May 28, 2024

(87) PCT Pub. No.: WO2023/099402
PCT Pub. Date: Jun. 8, 2023

(65) Prior Publication Data
US 2025/0050059 A1     Feb. 13, 2025

(30) Foreign Application Priority Data
Dec. 1, 2021     (EP) ..................................... 21211835

(51) Int. Cl.
*A61M 25/00*          (2006.01)
(52) U.S. Cl.
CPC ................................. *A61M 25/002* (2013.01)
(58) Field of Classification Search
CPC ... B65D 5/18; B65D 5/20; B65D 5/02; B65D 5/0015; B65D 5/00; A61M 25/002
(Continued)

(56) References Cited

U.S. PATENT DOCUMENTS 1,483,195 A * 2/1924 Pinkerton .............. B65D 5/528
206/730
4,700,831 A * 10/1987 Kassai ................. B65D 5/4237
229/162.1
(Continued)

FOREIGN PATENT DOCUMENTS

WO     2006120452 A1     11/2006
WO     2008078397 A1     7/2008
WO     2015023702 A1     2/2015

OTHER PUBLICATIONS

International Search Report from the corresponding International Patent Application No. PCT/EP2022/083479, dated Feb. 21, 2023.

*Primary Examiner* — Chun Hoi Cheung
(74) *Attorney, Agent, or Firm* — Greer, Burns & Crain, Ltd.; Steven P. Fallon

(57)          ABSTRACT

A preferred embodiment folding box includes a bottom. A circumferential lateral wall is connected to the bottom. A lid is hinged to the rear wall portion, so that the lid is pivotable in an open state of the folding box and closed state. A panel of the wall includes two front flaps each being connected to the panel via a first crease. In the closed state of the folding box, a slot is delimited by a front wall portion, an edge region and the two front flaps. A slot is arranged between the edge region and the front wall portion in the closed state to allow insertion of a package information leaflet. The wing is integrally connected to the front wall portion via a second crease and configured to protrude from the front wall portion along the panel of the lid when the folding box is in the closed state.

11 Claims, 3 Drawing Sheets

(58) Field of Classification Search
USPC ..... 229/122, 125.05, 125.41, 931, 118, 121;
206/232, 0.815, 364, 831
See application file for complete search history.

(56)                  References Cited

U.S. PATENT DOCUMENTS

| | | | | | |
|---|---|---|---|---|---|
| 5,860,589 | A * | 1/1999 | Hsu | ...................... | B65D 5/4204 |
| | | | | | 229/921 |
| 6,913,140 | B2 * | 7/2005 | Lo Duca | .............. | B65D 5/5014 |
| | | | | | 229/120.08 |
| 6,923,366 | B2 * | 8/2005 | Lo Duca | .............. | B65D 5/4237 |
| | | | | | 206/232 |
| 6,971,511 | B2 * | 12/2005 | Holmon | .............. | B65D 5/4204 |
| | | | | | 206/232 |
| 7,036,715 | B2 * | 5/2006 | Lo Duca | .............. | B65D 5/4237 |
| | | | | | 206/232 |
| 8,910,784 | B2 * | 12/2014 | Moore | ................ | B65D 5/4204 |
| | | | | | 206/273 |
| 9,108,781 | B2 * | 8/2015 | Albrecht | ................ | B65D 5/701 |
| 2002/0117409 | A1 * | 8/2002 | Okin | ...................... | B65D 5/528 |
| | | | | | 206/730 |
| 2004/0020977 | A1 * | 2/2004 | Lo Duca | .............. | B65D 5/4237 |
| | | | | | 206/232 |

* cited by examiner

HINGED LID FOLDING BOX FOR CATHETER SYSTEMS

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2022/083479, which was filed Nov. 28, 2022, which application claimed priority from EP Application 21211835.0, which was filed Dec. 1, 2021.

FIELD OF THE INVENTION

The present invention relates to a folding box for enclosing a medical device, a folding box arrangement and a method for packaging a medical device.

BACKGROUND

When packaging and thereafter transporting packaged medical devices, a package information leaflet is usually provided for each medical device, which leaflet is usually put into a transparent envelope that is attached to an outside of the package or the leaflet is put into the packaging prior to closing the package. However, during global transport the envelope and the information contained therein can get lost. Furthermore, providing the envelope and arranging the leaflet therein requires additional material and effort. Also, the envelope is aesthetically deficient and thus not promotional.

Furthermore, the information leaflet is selected from a plurality of package information leaflets depending on a destination of delivery of the medical device, called "country specific labeling".

During production and packaging it's very often not known, where the device will be shipped, so having the option to insert a (country) specific leaflet in the finally packed and closed folding box of the device gives huge flexibility in the whole distribution process.

SUMMARY OF THE INVENTION

A preferred embodiment folding box for enclosing a medical device is disclosed. The folding box includes a bottom. A circumferential lateral wall is connected to the bottom. A lateral wall includes a front wall portion and an opposing rear wall portion. A lid is hinged to the rear wall portion, so that the lid is pivotable in an open state of the folding box. The lid is configured to be connected to the circumferential lateral wall in a closed state of the folding box to prevent pivoting open of the lid. The lid includes an edge region, wherein the lid includes a panel forming the edge region, the panel extending opposite the bottom in the closed state of the folding box. The panel includes two front flaps each being connected to the panel via a first crease, wherein the edge region is arranged between the two front flaps, wherein the two front flaps are configured to be connected to an outside of the front wall portion in the closed state of the folding box such that the slot is delimited by the front wall portion, the edge region and the two front flaps. A slot is arranged between the edge region and the front wall portion in the closed state of the folding box to allow insertion of a package information leaflet through the slot into an internal space of the folding box. The wing is integrally connected to the front wall portion via a second crease and configured to protrude from the front wall portion along the panel of the lid when the folding box is in the closed state.

Preferably, the bottom and the panel can be congruential and/or rectangular, respectively.

BRIEF DESCRIPTION OF THE DRAWINGS

In the following, embodiments of the present invention as well as further features and advantages of the present invention are described with reference to the Figures, wherein.

DETAILED DESCRIPTION OF THE PREFERRED EMBODIMENTS

Figure 1:
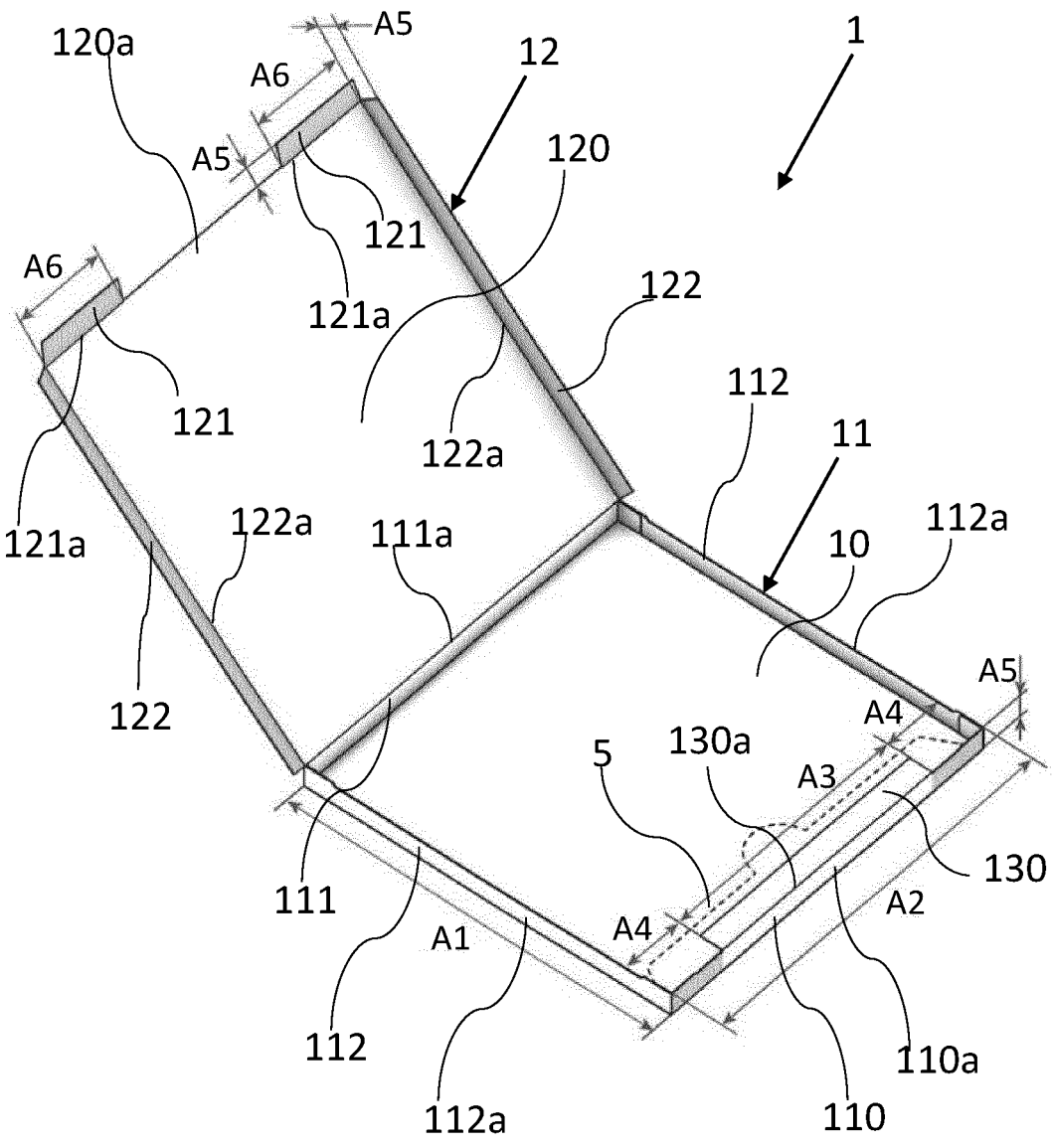
FIG. 1 shows an embodiment of a folding box according to the present invention in an open state in which a lid of the folding box is pivoted away from a bottom of the folding box to expose the internal space of the folding box.

In a preferred embodiment folding box for enclosing a medical device, due to the respective crease connecting the respective front flap to the panel of the lid of the folding box, the respective front flap can be folded/pivoted towards the outside of the front wall portion of the lateral wall of the folding box (e.g. to glue the respective front flap to the outside of the front wall portion upon closing the folding box).

This prevents that the package information leaflet gets entangled with an object (e.g. a packaged medical device) arranged in the internal space of the folding box, since the wing is configured to be arranged on top of this object when the object resides in the internal space. Also, the wing hinders the leaflet, once inserted into the folding box, to fall out of the box again due to the restoring force of the material as the wing tends to bend backwards against the lid and thereby closes the slot. Further, the wing guides the leaflet into the internal space of the folding box.

According to an embodiment, the lid is integrally connected to the rear wall portion and hinged to the rear wall portion via a crease. This allows to pivot the lid in order to open and close folding box. Further, in an embodiment, the edge region of the lid is arranged opposite the crease.

In an embodiment, in the closed state of the folding box, each front flap is configured to be connected to the outside of the front wall portion by an adhesive.

Preferably, in an embodiment, an upper side of the wing and a bottom side of the edge region form a guide for guiding the package information leaflet when the package information leaflet is inserted into the internal space of the folding box through the slot. Particularly, this further prevents that the package information leaflet gets entangled with an object (e.g. a packaged medical device) arranged in the internal space of the folding box. Also, the wing and the lid in cooperation hinder the leaflet, once inserted into the folding box, to fall out of the box again due to the restoring force of the material as the wing tends to bend backwards against the lid and thereby closes the slot.

Further, in an embodiment, the circumferential lateral wall further includes two opposing side wall portions connecting the front wall portion to the rear wall portion.

Particularly, in an embodiment, each side wall portion is connected to the rear wall portion and to the front wall portion by an adhesive.

Furthermore, according to an embodiment, the lid includes two opposing side flaps, each side flap connected to the panel via a crease, each side flap configured to be connected to an outside of an associated side wall portion in the closed state of the folding box.

Furthermore, in an embodiment, in the closed state of the folding box, each side flap is configured to be connected to the outside of the associated side wall portion by an adhesive.

According to a further embodiment, in the closed state, the folding box is an orthorhombic folding box.

Further, in an embodiment, in the closed state, a height of the box in a direction normal to the bottom of the folding box is smaller than an extension of the folding box in a plane perpendicular to the direction.

According to an embodiment, the folding box can be formed out of one of the following materials: card stock, corrugated fiberboard, paperboard or plastics. Particularly, for closing the folding box card stock, corrugated fiberboard and paperboard are suitable.

Any other suitable, particularly foldable, sheet material can also be used.

A further aspect of the present invention relates to a folding box arrangement, including a folding box according to the present invention, the folding box being in the closed state (particularly with the front and side flaps connected, particularly by means of an adhesive, to the lateral wall), the folding box arrangement further including a sterile medical device enclosed in a packaging, the packaging and the medical device therein being arranged in the internal space of the folding box, and wherein the folding box arrangement further includes a package information leaflet arranged in the internal space of the folding box between the lid and the medical device.

According to a preferred embodiment of the arrangement, the medical device is a catheter.

According to yet another aspect of the present invention, a method for packaging a medical device using a folding box according to the present invention is disclosed, the method including the steps of:

providing a medical device in the internal space of the folding box and closing the folding box by connecting the lid to the circumferential lateral wall to bring the folding box into its closed state, and inserting a package information leaflet through the slot into the internal space of the folding box with the folding box being in the closed state.

According to an embodiment of the method, closing the folding box includes connecting the front flaps to the outside of the front wall portion, particularly by means of an adhesive, and/or connecting each side flap to the outside of the associated side wall portion of the circumferential lateral wall of the folding box, particularly by means of an adhesive.

Furthermore, according to an embodiment of the method, before inserting the package information leaflet through the slot into the internal space of the folding box, the package information leaflet is selected from a plurality of package information leaflets depending on a destination of delivery of the medical device residing in the internal space of the folding box.

A further aspect of the present invention relates to the use of the folding box according to the present invention for enclosing a medical device. Preferably, to the use of the folding box for enclosing a medical device and a leaflet.

Figure 2:
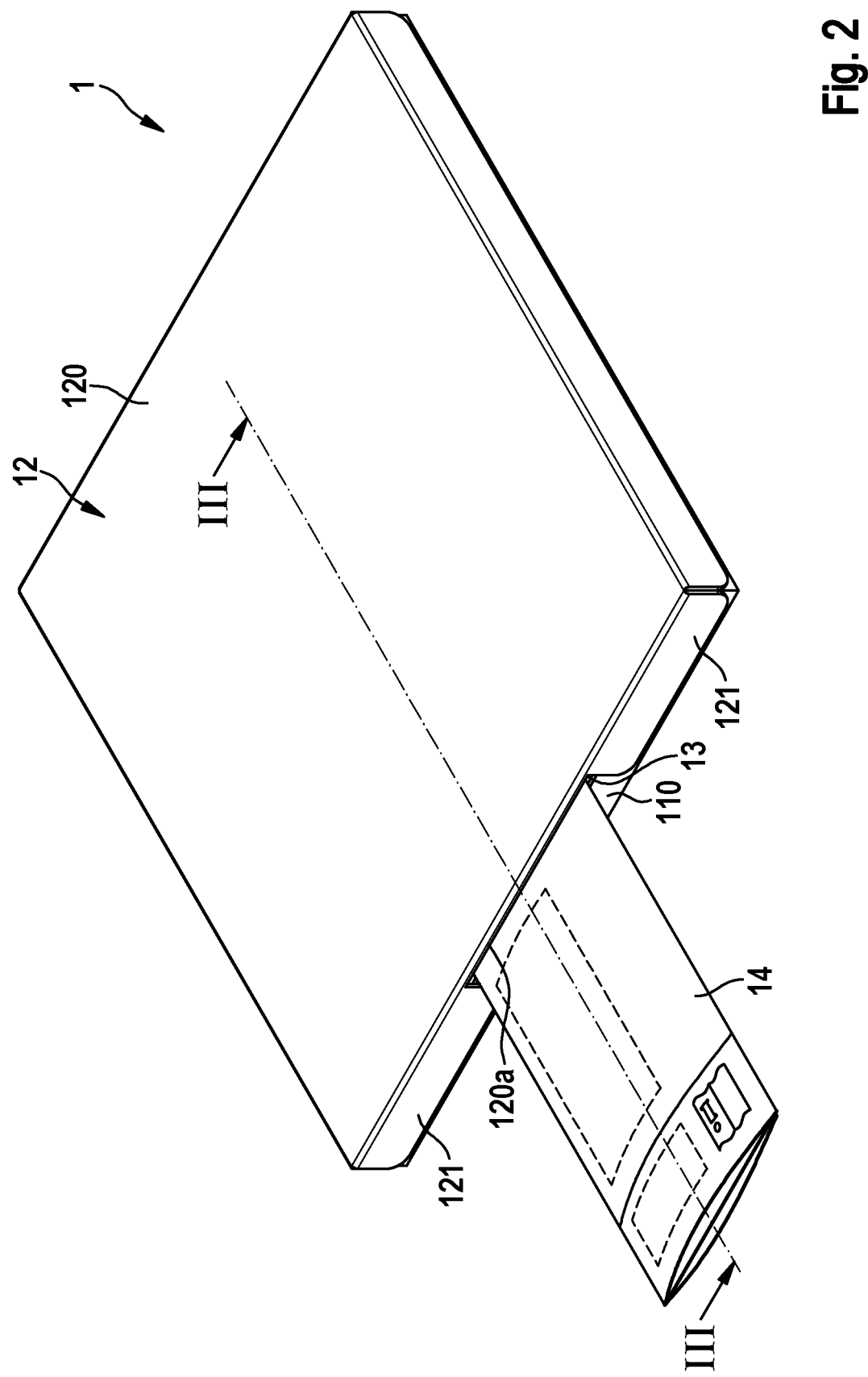
FIG. 2 shows the box of FIG. 1 in a closed state.
Figure 3:
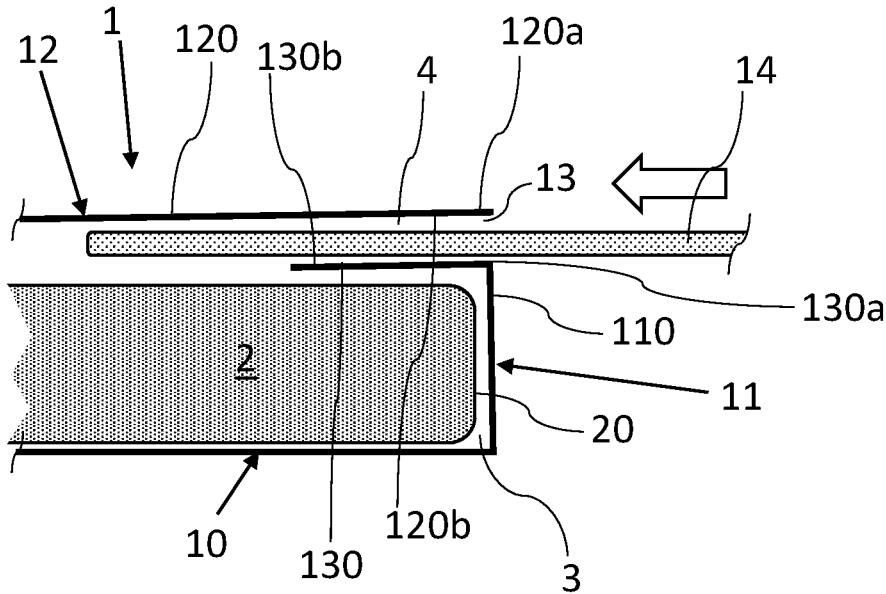
FIG. 3 shows a schematic cross-sectional view of a section of the closed folding box along plane III-III depicted in FIG. 2.

FIG. 1 shows in conjunction with FIGS. 2 and 3 an embodiment of a folding box 1 of the present invention for packaging a medical device 2 (cf. FIG. 3). The medical device 2 can be sterilized and enclosed in a surrounding packaging 20 (e.g. a bag formed out of plastic material) to maintain the sterile state of the medical device 2. However, a folding box 1 according to the present invention can also be used to package objects other than medical devices.

As indicated in FIGS. 1 to 3, the folding box 1 includes a bottom 10, particularly rectangular in shape and a circumferential lateral wall 11 connected to the bottom 10 on all four sides of the bottom 11. Particularly, the lateral wall 11 includes a front wall portion 110 being integrally connected to the bottom 10 and an opposing rear wall portion 111 being integrally connected to the bottom 10, too.

Furthermore, the folding box 1 includes a lid 12 hinged to the rear wall portion 111, so that the lid 12 is pivotable in an open state of the folding box 1, wherein the lid 12 is configured to be connected to the lateral wall 11 in a closed state of the folding box 1 to prevent pivoting open of the lid 12. Preferably, the lid 12 includes a panel 120 that is integrally connected to the rear wall portion 111 via a crease 111a, the lid 12 configured to cover an internal space 3 of the folding box 1. Furthermore, the lid 12 preferably includes two front flaps 121 on either side of an edge region 120a of the panel 120, the front flaps 121 protruding from the panel 120 and being integrally connected to the panel 120 via a crease 121a, respectively. Furthermore, the lid 12 preferably includes two side flaps 122 on opposing sides of the panel 120, each side flap 122 being integrally connected to the panel via a crease 122a.

When the lid 12 is closed by pivoting the panel 120 of the lid 12 downwards (towards the bottom 10), the front flaps 121 and side flaps 122 can be folded downwards and can be connected to the lateral wall 11 by means of a suitable adhesive. Particularly, the front flaps 121 are each connected to an outside 110a of the front wall portion, and the side flaps 122 are each connected to an outside 112a of an associated side wall portion 112 of the lateral wall 11 by means of the adhesive. After this procedure, the folding box 1 is in the closed state, wherein particularly re-opening the folding box 1 would require destroying the folding box 1 and/or undoing the connections formed using the adhesive.

Particularly, each wall portion 110, 111, 112 is integrally connected to the bottom 10 and folded upwards to form the lateral wall 11. The four wall portions 110, 111, 112 are preferably connected to one another in the corner regions of the lateral wall 11 by means of a suitable adhesive.

According to the present invention, the folding box 1 is configured such that in the closed state (in which the front and side flaps 121, 122 are preferably glued to the lateral wall 120), the folding box 1 includes a slot 13 arranged between the edge region 120a of the panel 120 and the front wall portion 110 to allow insertion of a package information leaflet 14 through the slot 13 into the internal space 3 of the folding box 1 as indicated in FIGS. 2 and 3.

Particularly, in the closed state of the folding box 1, the slot 113 remains open, and is delimited by the front wall portion 110, the edge region 120a and the two front flaps 121 between which the slot 113 extends.

Furthermore, preferably, as indicated in FIGS. 1 and 3, the folding box 1 preferably includes a wing 130, e.g. rectangular in shape, being integrally connected to an upper edge of the front wall portion 110 via a crease 130a and configured to protrude from the front wall portion 110 along the panel 120 of the lid 12 when the folding box 1 is in the closed state. In this way, an upper side 130b of the wing 130 and a bottom side 120b of the edge region 120a of the panel 120 of the lid 12 form a guide 4 configured to guide the package information leaflet 14 when the package information leaflet 14 is inserted into the internal space 3 of the folding box 1 through the slot 13 in the closed state of the folding box 1 so that the leaflet 14 does not become entangled with a content of the internal space 3 of the folding box 1. This is achieved by having the wing 130 overlap the content (e.g. a medical device 2 in an enclosing package 20) in the vicinity of the slot 13 so that the leaflet 14 is guided past an edge of the content and does not become entangled.

Further, in an embodiment, a height A5 of the folding box 1 in a direction normal to the bottom 10 of the folding box 1 is smaller than an extension A1, A2 of the folding box 1 in a plane perpendicular to the direction. In general, the dimensions of the folding box 1 can be adapted to the object that is to be packaged. As an example, the dimensions A1 to A6 stated in FIG. 1 can be selected as follows (stated in mm [millimeter] in each case): A1=240±1, A2=240±1, A3=160±1, A4=40±1, A5=15±1, A6=60±1.

Furthermore, in an embodiment, the bottom 10 can include a perforation 5 (e.g. at the front wall portion 110) to allow opening the folding box 1 along the perforation for taking a content (e.g. medical device 2 in package 20) out of the internal space 3 of the folding box when the folding box is in the closed state with the flaps 121, 122 glued to the lateral wall 11 as described above.

Furthermore, the folding box 1 can be formed out of one of the following materials: card stock, corrugated fiberboard, paperboard. Any other suitable, particularly foldable, sheet material can also be used such as plastics.

Due to the invention, product inserts such as package information leaflets 14 can be inserted into the folding box 1 through the slot 13 after the gluing process is complete and the folding box is in its closed state. This offers advantages in that the products do not have to be provided with country-specific product inserts during the final packaging process. Products can thus be produced generically, stored in the global distribution center, and only provided with product inserts before being shipped to specific destinations/markets.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A folding box for enclosing a medical device, the folding box comprising:
   a bottom,
   a circumferential lateral wall connected to the bottom, the lateral wall comprising a front wall portion and an opposing rear wall portion,
   a lid hinged to the rear wall portion, configured such that the lid is pivotable in an open state of the folding box, the lid configured to be connected to the lateral wall in a closed state of the folding box to prevent pivoting open of the lid, and wherein the lid comprises panel forming an edge region, the panel extending opposite the bottom in the closed state of the folding box, wherein the panel comprises two front flaps each being connected to the panel via a first crease, wherein said edge region is arranged between said two front flaps, wherein the two front flaps are configured to be connected to an outside of the front wall portion in the closed state of the folding box such that a slot is delimited by the front wall portion, said edge region and the two front flaps, wherein the slot is arranged between said edge region and the front wall portion in the closed state of the folding box configured to allow insertion of a package information leaflet through the slot into an internal space of the folding box, and
   a wing integrally connected to the front wall portion via a second crease and configured to protrude from the front wall portion along the panel of the lid when the folding box is in the closed state.

2. The folding box according to claim 1, wherein the lid is integrally connected to the rear wall portion and hinged to the rear wall portion via a third crease.

3. The folding box according to claim 2, wherein the edge region of the lid is arranged opposite the third crease.

4. The folding box according to claim 1, wherein an upper side of the wing and a bottom side of said edge region form a guide for guiding the package information leaflet when the package information leaflet is inserted into the internal space of the folding box through said slot.

5. The folding box according to claim 1, wherein the circumferential lateral wall further comprises two opposing side wall portions connecting the front wall portion to the rear wall portion.

6. The folding box according to claim 1, wherein the lid comprises two opposing side flaps, each side flap connected to the panel via a crease, each side flap configured to be connected to an outside of an associated side wall portion in the closed state of the folding box.

7. The folding box according to claim 1, being in the closed state, comprising a sterile medical device enclosed in a packaging, the packaging and the medical device therein being arranged in the internal space of the folding box, and wherein the folding box arrangement further comprises a package information leaflet arranged in the internal space of the folding box between the lid and the medical device.

8. The folding box according to claim 7, wherein the medical device is a catheter.

9. A method for packaging a medical device using a folding box according to claim 1, the method comprising the steps of:
   providing a medical device in the internal space of the folding box and closing the folding box by connecting the lid to the circumferential lateral wall, and
   inserting a package information leaflet through the slot into the internal space of the folding box.

10. The method according to claim 9, wherein closing the folding box comprises connecting the second flaps to the outside of the front wall portion and/or connecting each side flap to the outside of the associated side wall portion of the circumferential lateral wall of the folding box.

11. The method according to claim 9, wherein before inserting the package information leaflet through the slot into the internal space of the folding box said package information leaflet is selected from a plurality of package information leaflets depending on a destination of delivery of the medical device residing in the internal space of the folding box.

* * * * *